(12) United States Patent
Kodama

(10) Patent No.: US 8,435,781 B2
(45) Date of Patent: May 7, 2013

(54) POROUS SHEET-FORM MATERIAL FOR CELL CULTURE, AND BIOREACTOR AND CULTURING METHOD UTILIZING SAME

(75) Inventor: Makoto Kodama, Fukuoka (JP)

(73) Assignee: Kyushu Institute of Technology, Fukuoka (JP)

( * ) Notice: Subject to any disclaimer, the term of this patent is extended or adjusted under 35 U.S.C. 154(b) by 1337 days.

(21) Appl. No.: 11/574,006

(22) PCT Filed: Aug. 12, 2005

(86) PCT No.: PCT/JP2005/014811
§ 371 (c)(1), (2), (4) Date: Feb. 20, 2007

(87) PCT Pub. No.: WO2006/019043
PCT Pub. Date: Feb. 23, 2006

(65) Prior Publication Data
US 2009/0017541 A1    Jan. 15, 2009

(30) Foreign Application Priority Data

Aug. 17, 2004   (JP) ................................ 2004-237002

(51) Int. Cl.
*C12M 1/14* (2006.01)
*C12M 3/04* (2006.01)
*C12M 1/00* (2006.01)
*C12M 3/00* (2006.01)

(52) U.S. Cl.
USPC .................. 435/299.1; 435/283.1; 435/289.1; 435/293.2; 435/299.2; 435/307.1

(58) Field of Classification Search ..... 435/283.1–309.4
See application file for complete search history.

(56) References Cited

U.S. PATENT DOCUMENTS 5,079,168 A * 1/1992 Amiot ........................ 435/297.2
5,266,476 A   11/1993 Sussman et al.
(Continued)

FOREIGN PATENT DOCUMENTS

EP   0240560 B1   10/1987
EP   1211309 A1   6/2002
(Continued)

OTHER PUBLICATIONS

Mizutani, S., 'Bioscience and Industry,' vol. 48, No. 4, p. 337-342 (1990) Japan.

(Continued)

*Primary Examiner* — Nathan Bowers
*Assistant Examiner* — Lydia Edwards
(74) *Attorney, Agent, or Firm* — Sughrue Mion, PLLC

(57) ABSTRACT

The present invention provides a bioreactor having a system that can grow cells, tissue, etc. while maintaining or improving their function, and finally recover the cells as they are with good efficiency. The bioreactor has a porous sheet-form material disposed in its main body, the porous sheet-form material being formed from a nonwoven fabric, etc. having high cell affinity in order to retain cells. This porous sheet-form material has a thermosensitive polymer and a cell-adhesive substance incorporated thereinto, and the porous sheet-form material is not only cell-adhesive but also allows cells and tissue to be detached from the porous sheet-form material as they are by, for example, cooling from 37° C. to 25° C. Furthermore, in order to efficiently ensure the bioactivity or the survival of the cells, it is arranged so that circulation of a culture medium in a culturing space of the bioreactor is of a radial flow type.

18 Claims, 5 Drawing Sheets

U.S. PATENT DOCUMENTS

Figure 1:
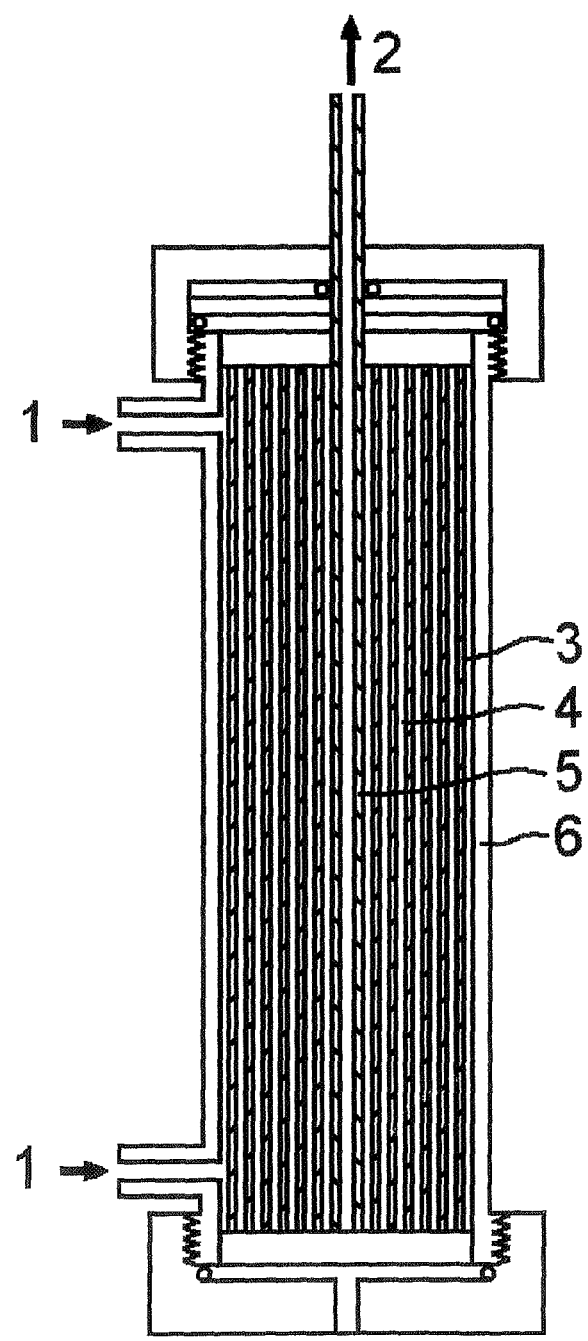

| | | | |
|---|---|---|---|
| 5,376,548 A | | 12/1994 | Matsuo et al. |
| 5,385,836 A | * | 1/1995 | Kimura et al. ............... 435/177 |
| 6,149,817 A | * | 11/2000 | Peterson et al. ............ 210/644 |
| 2003/0036196 A1 | * | 2/2003 | Okano et al. ................. 435/373 |

FOREIGN PATENT DOCUMENTS

| | | |
|---|---|---|
| JP | 62-122586 A | 6/1987 |
| JP | 02-211865 A | 8/1990 |
| JP | 03-292882 A | 12/1991 |
| JP | 05-038278 A | 2/1993 |
| JP | 05-244938 A | 9/1993 |
| JP | 05-276923 A | 10/1993 |
| JP | 2001-136960 A | 5/2001 |

OTHER PUBLICATIONS

European Search Report in corresponding European Application No. 05770651.

\* cited by examiner

POROUS SHEET-FORM MATERIAL FOR CELL CULTURE, AND BIOREACTOR AND CULTURING METHOD UTILIZING SAME

TECHNICAL FIELD

The present invention relates to a system for culturing a microorganism or part of an organism, such as useful cells, in a bioreactor while maintaining or enhancing their function, and subsequently recovering the cells and/or cell secretions as they are.

BACKGROUND ART

Many conventional methods for growing and recovering cells have been proposed. However, almost all of the methods employ a dish (culture dish), and the number of cells that can be grown is limited. Furthermore, when a thermosensitive polymer is used as a culture substrate, cells grow and are recovered in the form of a sheet or a spheroid within or over a polymer gel, which is different from the actual state in which cells exist. Methods for recovering cultured cells by virtue of a change in environmental temperature using a thermosensitive polymer are described in detail in, for example, Patent Publications 1 to 3.
(Patent Publication 1) JP-A-2-211865 (JP-A denotes a Japanese unexamined patent application publication.)
(Patent Publication 2) JP-A-5-38278
(Patent Publication 3) JP-A-5-244938

Furthermore, with regard to a method for culturing cells using a bioreactor, since in many conventional methods the flow of a supplied culture medium is not of a radial flow type, if a large amount of tissue such as bacteria or cells is immobilized, it is difficult to supply sufficient nutrient and oxygen, control of their concentration is also difficult, and it is therefore difficult to avoid the tissue such as bacteria or cells necrotizing. A radial flow type bioreactor has been introduced in, for example, Non-Patent Publication 1 below.
(Non-Patent Publication 1) S. Mizutani, 'Bioscience and Industry', Vol. 48, No. 4, p. 337-342 (1990)

The present inventors have also proposed that the cell adhesion and biocompatibility of a cell culture membrane can be improved by, for example, hydrophilizing the surface of a porous sheet-form material using a polyamino acid urethane copolymer (Patent Publication 4). However, a way in which these conventional techniques could be combined in order to totally overcome various problems of the conventional techniques has not been examined or proposed.
(Patent Publication 4) JP-A-2001-136960

DISCLOSURE OF THE INVENTION

Problems to be Solved by the Invention

It is an object of the present invention to solve the above-mentioned problems of the conventional techniques, and to therefore provide a bioreactor comprising means for immobilizing cells (including tissue or microorganism) to a porous sheet-form material having incorporated therewith a cell-adhesive thermosensitive polymer, and means for supplying, with good efficiency, a culture medium, in order to maintain the bioactivity of the cells, together with means for separating and recovering the cells as they are by virtue of a change in configuration of the thermosensitive polymer by changing the culture medium temperature after activating or growing the cells, and/or means for separating and recovering cell secretions, and a cell culturing method employing same.

Means for Solving the Problems

One embodiment of the present invention is a radial flow type bioreactor as below. That is, as shown in FIG. 1, it is a radial flow type bioreactor comprising, within a tubular reactor main body 6, a culturing space housing a culture medium-recovering porous tube 5, spacers 4, and a porous sheet-form material 3 provided between the spacers, the porous sheet-form material 3 allowing cells to adhere and to pass through, wherein this reactor is formed so that a culture medium supplied from at least one culture medium inlet port 1 formed in the reactor main body 6 flows through the culturing space and the culture medium-recovering porous tube 5 and flows out from a culture medium outlet port 2 communicating with one end of the porous tube 5, the porous tube 5 and the spacers 4 allow cells to pass through, and the porous sheet-form material 3 has its surface, which is hydrophilized, covered with a thermosensitive polymer layer.

The bioreactor of the present invention is operated by a method such as that below, and cells are cultured or grown.

In this bioreactor, cells are made to adhere or attach to the porous sheet-form material, the cells are grown or cultured while supplying a culture medium to at least one culture medium inlet port formed in the reactor main body, passing it through the culturing space and then through the culture medium-recovering porous tube, and making the culture medium flow out from the culture medium outlet port communicating with one end of the porous tube, and subsequently the cells and/or cell secretions are recovered by destroying the thermosensitive polymer layer of the porous sheet-form material under conditions in which the temperature is higher or lower than the culture temperature.

Another embodiment of the present invention relates to a porous sheet-form material for cell culture, the porous sheet-form material forming a module suitably used in the bioreactor, and a culturing method, wherein the porous sheet-form material has its surface, which is hydrophilized, covered with a thermosensitive polymer layer. This porous sheet-form material for cell culture is itself one embodiment of the present invention, and desirable results can be obtained even when it is used in a bioreactor other than the radial flow type bioreactor of the present invention. The cells referred to in the present invention include tissue formed from a plurality of cells, and a living body such as a microorganism.

Effects of the Invention

In accordance with the present invention, it is possible to culture or grow a large number of cells and stably recover the cultured or grown cells. Use of the present invention therefore enables stem cells, which have been difficult to grow and have posed a problem, to be grown, thereby contributing to regenerative medicine, tissue engineering, or bioindustries employing cells.

BRIEF DESCRIPTION OF DRAWINGS (FIG. 1) A view showing the internal structure of one example of the bioreactor of the present invention.
(FIG. 2) A schematic drawing for explaining a state in which a porous sheet-form material and spacers are housed within a main body of the bioreactor of the present invention.
(FIG. 3) A diagram showing the results of measurement of oxygen consumption rate.

(FIG. 4) A diagram showing the results of measurement of albumin secretion rate.

Figure 5:
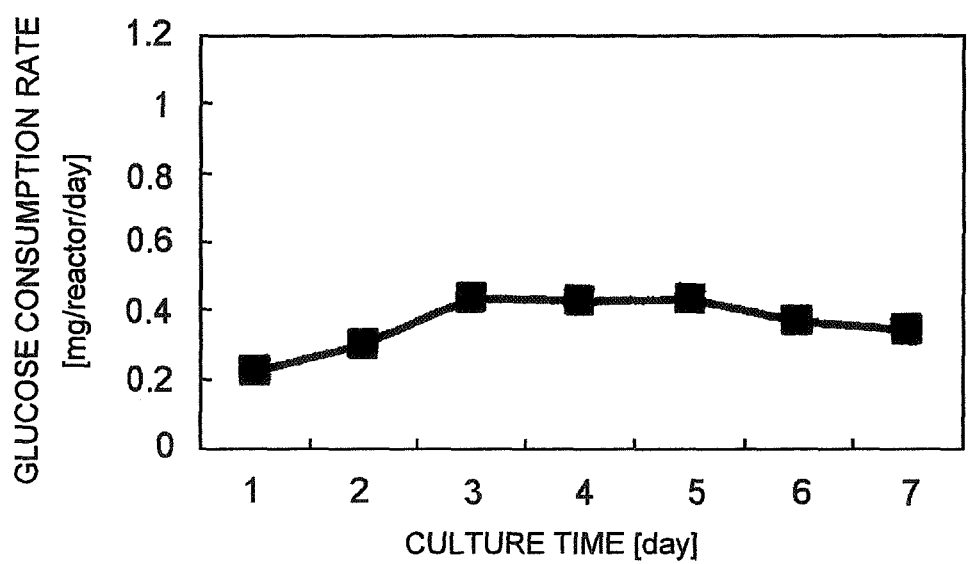

(FIG. 5) A diagram showing the results of measurement of glucose consumption rate.

EXPLANATION OF REFERENCE NUMERALS AND SYMBOLS

1 Culture medium inlet port
2 Culture medium outlet port
3 Porous sheet-form material
4 Spacer
5 Culture medium-recovering porous tube
6 Reactor main body

BEST MODE FOR CARRYING OUT THE INVENTION

The porous sheet-form material of the present invention allows cells to adhere and to pass through, and has its surface, which is hydrophilized, covered with a thermosensitive polymer layer. The porous sheet-form material referred to here is not particularly limited in terms of material and configuration as long as it allows cells to adhere and to pass through, but it is preferable to use a porous nonwoven fabric formed from a known organic polymer, for example, a fluorine-containing polymer such as PTFE, a polyolefin, a polyester, a polyurethane, a cellulose fiber, a regenerated cellulose fiber, a polyamide, or a polyimide.

Since the porous sheet-form material of the present invention has a pore size sufficient for cells to pass through, cells can move, and even when a large quantity of cells, microorganisms, or tissue is retained, it is resistant to clogging. The pore size is at least 200 μm, and preferably on the order of 200 to 500 μm.

The porous sheet-form material of the present invention has its surface hydrophilized and covered with a thermosensitive polymer layer, but the hydrophilization method/means is not particularly limited. When the porous sheet-form material is formed from an intrinsically hydrophilic polymer, it need not particularly be subjected to a hydrophilization treatment. It is preferable to treat the surface of the porous sheet-form material with a polyamino acid/urethane copolymer (ref. Patent Publication 4), a protein such as collagen, gelatin, albumin, or fibronectin, a hydrogel, etc. in order to carry out hydrophilization and promote cell adhesion.

The porous sheet-form material whose surface has been hydrophilized has the top thereof further covered and treated with a thermosensitive polymer layer. The thermosensitive polymer layer may be formed from a thermosensitive polymer on its own, or may be a mixture or a chemical reaction product between a thermosensitive polymer and a cell-adhesive substance. The state of the covering may be a coating with a thermosensitive polymer, a coating with a mixture or a chemical reaction product between a cell-adhesive substance and a thermosensitive polymer, chemical bonding of a thermosensitive polymer to the hydrophilized surface, or chemical bonding of a cell-adhesive substance to the hydrophilized surface. The covering may be partial.

The thermosensitive polymer referred to in the present invention means a polymer that undergoes phase transfer from a sol to a gel or a gel to a sol by heating or cooling. After completion of cell culturing, by merely changing the temperature from, for example, 37° C. to 25° C. or lower, a gel-form thermosensitive polymer layer turns into a sol form, thus enabling cells that have grown to be peeled off and recovered.

The thermosensitive polymer used in the present invention desirably has a phase transfer temperature of 0° C. to 80° C., and preferably 0° C. to 50° C. When the temperature exceeds 80° C., there is a possibility of the cells perishing, and when the temperature is lower than 0° C., the cell growth rate generally decreases to a great degree or the cells might perish, which is undesirable.

The thermosensitive polymer is known from Patent Publication 2, etc., and may be produced by, for example, polymerization or copolymerization of the monomers below. That is, it is a polymer or a copolymer of a (meth)acrylamide compound such as acrylamide or methacrylamide, an N-alkyl substituted (meth)acrylamide derivative such as N-ethylacrylamide, N-n-propylacrylamide, N-n-propylmethacrylamide, N-isopropylacrylamide, N-isopropylmethacrylamide, N-cyclopropylacrylamide, N-cyclopropylmethacrylamide, N-ethoxyethylacrylamide, N-ethoxyethylmethacrylamide, N-tetrahydrofurfurylacrylamide, or N-tetrahydrofurfurylmethacrylamide, or an N,N-dialkyl substituted (meth)acrylamide derivative such as N-ethyl-N-methylacrylamide or N,N-diethylacrylamide. A polymer of N-isopropylacrylamide is particularly preferable.

The cell-adhesive substance referred to is a natural or synthetic substance having cell adhesiveness. Examples of the natural substance include oligosaccharide, gelatin, collagen, fibronectin, laminin, fibrin, and a cell-adhesive peptide, which is a component of the above substances. Examples of the synthetic substance include a homopolymer or copolymer of monomers containing a cell-adhesive group, or a copolymer of a monomer containing a cell-adhesive group and a monomer that does not contain one. Examples of the cell-adhesive group include a carboxylic acid group and a salt thereof, an anhydride, a sulfonic acid group and a salt thereof, a sulfonic acid ester, a sulfonamide, a phosphoric acid group and a salt thereof, an amino group, a hydroxyl group, a long-chain alkyl group, a mercapto group, an ether group, a thioether group, a polyether group, a ketone group, an aldehyde group, an acyl group, a cyano group, a nitro group, an acylamino group, a halogen group, a glycidyl group, and an allyl group.

The culture medium-recovering porous tube of the present invention has pores that enable a culture medium and cells to pass through adequately, and a culture medium supplied from a culture medium inlet port passes through the culturing space and then through the culture medium-recovering porous tube, and flows out from a culture medium outlet port communicating with one end of the culture medium-recovering porous tube. The material and shape of the culture medium-recovering porous tube are not particularly limited, and it is preferable to form it from, for example, a polyethylene or poly-4-fluoroethylene resin in the form of a tube along the central axis of a reactor main body.

The porous sheet-form material of the present invention is incorporated into a bioreactor module in a culturing space of the bioreactor by, for example, winding it in a spiral around a culture medium-recovering porous tube. In this process, in the present invention, a spacer is used in order to protect the porous sheet-form material to which cells adhere or are attached or to prevent the porous sheet-form material from sticking to each other.

The material and shape of the spacer are not particularly limited as long as the above-mentioned object is attained and the passage of cells and culture medium is not interfered with. Examples thereof include a porous film of a known organic polymer, a porous woven/knitted or nonwoven fabric of a fiber, a plastic net, a rod, and a wire, which may be used singly or in combination. In the case of the rod, about 10 to 300 rods may be used. It is necessary for the porous film or the porous woven/knitted or nonwoven fabric to allow cells to pass through, and it is desirable that the pore size is normally on the order of 200 to 1,000 μm. In the present invention, it is particularly convenient in terms of handling if a porous spacer such as a woven/knitted or nonwoven fabric of a fiber and the porous sheet-form material are superimposed and used. In the present invention, the spacer also has a function as a filler for fixing the porous sheet-form material in the culturing space of the bioreactor.

The bioreactor of the present invention is explained below by reference to drawings. As shown in FIG. 1, the bioreactor main body 6 houses a culture medium-recovering porous tube 5 for a culture medium to flow out from, a porous sheet-form material 3 that enables the culture medium and cells to pass through and the cells to adhere to and grow on the surface thereof singly or as an aggregate, and a tube or a nonwoven fabric etc. 4, which functions as a spacer. The material, shape, etc. of the bioreactor main body are not particularly limited, but it is desirable for it to have a tubular shape such as a cylindrical shape or a rectangular tube shape. The culture medium-recovering porous tube 5 has a pore size that allows a liquid such as a culture medium and cells to pass through freely, and normally has a pore size of 200 to 2,000 μm. It is preferable for the spacer to be fixed in parallel to the central axis of the reactor main body. The number of culture medium inlet ports 1 formed in the reactor main body may be 1 or 2 or greater, but is normally 1 to 6, preferably 2 to 4, and particularly preferably 2. When a plurality of culture medium inlet ports are formed, it is preferable to form them at symmetrical positions relative to the center in the axial direction of the reactor main body. Although not shown in the figure, in the bioreactor, the culture medium inlet port 1 is connected to a culture medium adjustment vessel or a culture medium tank via a pump, and the culture medium outlet port 2 is connected to the same culture medium adjustment vessel or culture medium tank via an oxygenation membrane. In the culture medium adjustment vessel, the pH, the dissolved oxygen concentration, etc. of the culture medium are adjusted.

Figure 2:
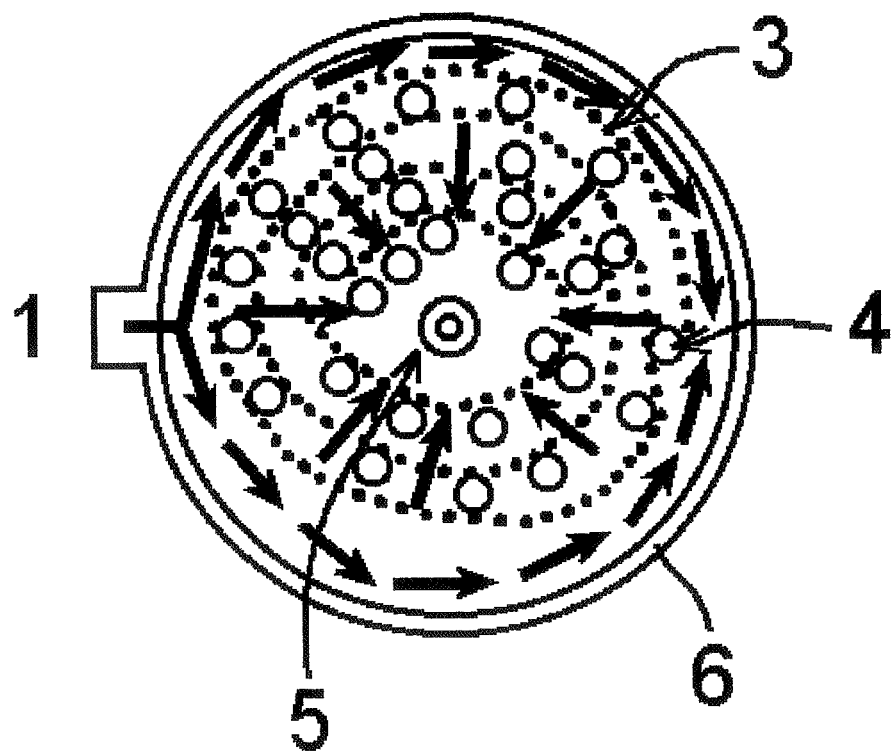
Figure 3:
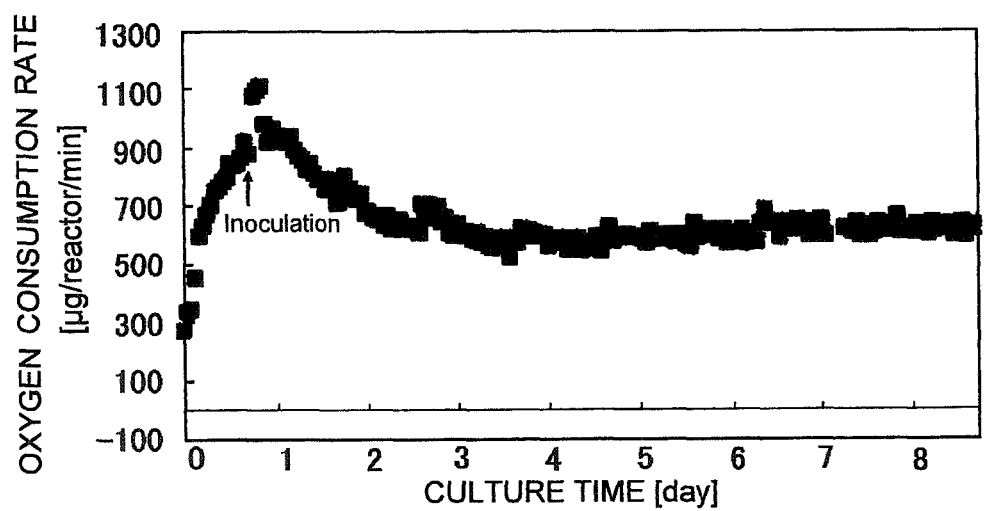

In FIG. 1, the porous sheet-form material is spirally wound as shown in FIG. 2 and is wound around the central axis of the reactor while sandwiching the spacer. The porous sheet-form material is incorporated into a module of the bioreactor in this way, and cells are cultured on the porous sheet-form material within the culturing space. There is a culturing space within the tubular reactor main body 6, which houses the culture medium-recovering porous tube 5, the spacer 4, and the porous sheet-form material 3 allowing cells to pass through, and the culture medium, which is supplied from at least one culture medium inlet port 1 formed in the reactor main body 6, is parted to either side in the culturing space as shown in FIG. 2 and forms a flow along the peripheral direction and a flow toward the culture medium-recovering porous tube 5 at the center (radial flow), and the culture medium then converges to the culture medium-recovering porous tube 5 at the center and flows out from the culture medium outlet port 2, which communicates with one end of the culture medium-recovering porous tube 5. The other end of the culture medium-recovering porous tube 5 is sealed, and the culture medium that has flowed into the culture medium-recovering porous tube 5 heads toward the culture medium outlet port 2. After passing from the culture medium adjustment vessel (not illustrated) through a pump (not illustrated), etc., the culture medium enters the culturing space from the culture medium inlet port 1, passes through the culture medium-recovering porous tube 5 at the center, the culture medium inlet port 2, the oxygenation membrane (not illustrated), etc., and returns to the culture medium adjustment vessel.

Since the porous sheet-form material of the present invention has its hydrophilized surface covered with the thermosensitive polymer layer, the thermosensitive polymer layer and cells can be peeled off from a substrate sheet of the porous sheet-form material by, for example, reducing the temperature of the culture medium to the vicinity of 25° C. after growing and immobilizing cells at 37° C. Such an operation enables cells to be peeled off as they are without any damage. For example, after the cells thus peeled off are taken out together with the culture medium, cell secretions, etc., they are respectively separated and purified by known appropriate methods. Alternatively, the porous sheet-form material with cultured/grown cells attached thereto is taken out, the cells are separated by virtue of the properties of the thermosensitive polymer by, for example, decreasing the temperature thereof outside the reactor, and the cells may be recovered by the use of a membrane and the porous sheet-form material may be washed.

In the present invention, the cells that are used are not in any way limited, and as a culture medium a wide variety of known liquids that enable cells to grow or cultured cells to grow, etc. may be used. Furthermore, the oxygen concentration, and the concentration of a nutrient such as glucose may be freely controlled.

The bioreactor of the present invention is a system that can be filled with cells with high efficiency as shown in FIG. 1 and FIG. 2 and can, moreover, maintain their activity. It is also a system that enables cells that have been grown and/or cell secretions to be easily recovered. The present invention is explained below in further detail by way of examples.

EXAMPLE 1

Figure 4:
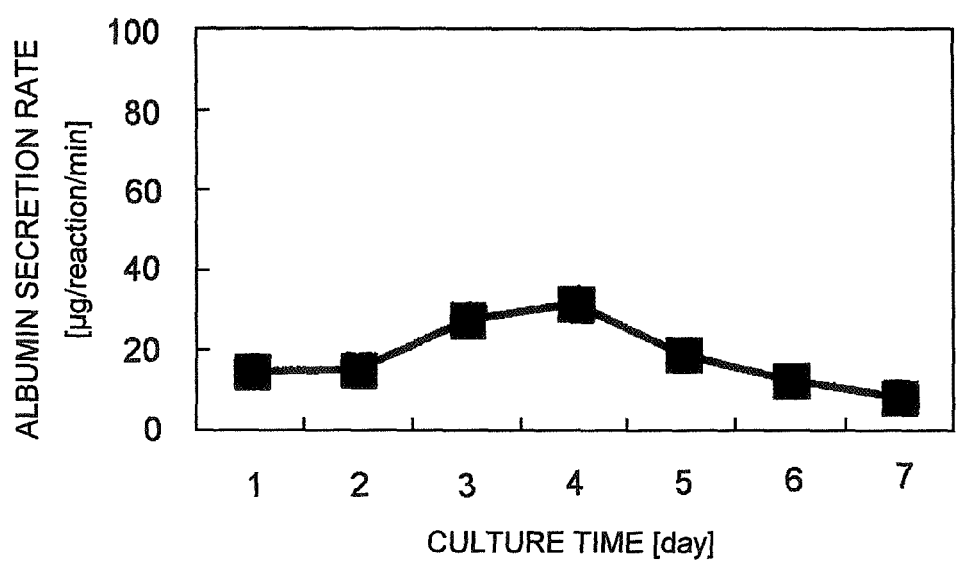

In the bioreactor shown in FIG. 1, hepatocytes were attached to the porous sheet-form material 3, and while supplying a culture medium capable of growing hepatocytes and containing no albumin from the culture medium inlet port 1, the hepatocytes were cultured within the culturing space at 37° C. An oxygen consumption rate and a secretion rate of albumin into the culture medium were measured. As is clear from the results shown in FIG. 3, there was a stable oxygen consumption for 8 days after inoculation. Furthermore, as shown in FIG. 4, secretion of albumin was observed for 7 days. On the 8th day, the cells were recovered by decreasing the temperature from 37° C. to 25° C., and $2 \times 10^8$ cells were recovered from $1 \times 10^9$ cells inoculated. The configuration of the cells was normal.

As the porous sheet-form material 3, a porous sheet-form material formed from PTFE treated with a polyamino acid/urethane copolymer, and as a thermosensitive polymer layer, NIPAM (poly-N-isopropylacrylamide) were used. As the spacer 4, a rayon fabric was used.

EXAMPLE 2

In the bioreactor shown in FIG. 1, L929 cells were attached to the porous sheet-form material 3, and while supplying a culture medium capable of growing L929 cells, L929 cells were cultured within the culturing space at 37° C. A glucose consumption rate was measured, and the results are given in FIG. 5. The glucose consumption rate increased until the third day, suggesting that the cells grew within the reactor while maintaining their activity.

EXAMPLE 3

In the bioreactor shown in FIG. 1, the porous sheet-form material 3 was inoculated with $1 \times 10^8$ CHO-K1 cells, the cells were cultured within the culturing space at 37° C. for 1 week while supplying a culture medium capable of growing CHO-K1 cells, and when the temperature was then decreased to 25° C., it was observed that the cells became detached. The recovery rate of the cells was 40%.

INDUSTRIAL APPLICABILITY

Use of the bioreactor of the present invention enables a large number of cells to be cultured or grown and the cells or cell secretions to be stably recovered. It is therefore possible to grow stem cells, which have been difficult to grow and have posed a problem, and it is thereby expected to contribute to regenerative medicine, tissue engineering, or bioindustries employing cells.

What is claimed is:

1. A radial flow type bioreactor comprising, within a tubular reactor main body (6), a culturing space housing a culture medium-recovering porous tube (5), a spacer (4), and a porous sheet-form material (3) provided between the spacers, wherein the reactor is formed so that a culture medium supplied from at least one culture medium inlet port (1) formed in the reactor main body (6) passes through the culturing space and the culture medium-recovering porous tube (5) and flows out from a culture medium outlet port (2) connecting with one end of the porous tube (5), the porous tube (5) and the spacer (4) allowing cells to pass through, and the porous sheet-form material (3) having its surface, which is hydrophilized with a polyamino acid/urethane copolymer so that the porous sheet-form material (3) has thereon the polyamino acid/urethane copolymer, covered with a thermosensitive polymer layer,
    wherein the culture medium-recovering porous tube (5) is a single tube formed along the central axis of a reactor main body (6),
    the porous sheet-form material (3) has a pore size of 200 to 500 μm, and
    the spacer (4) comprises a plurality of plastic rods or a fibrous nonwoven fabric.

2. The bioreactor according to claim 1, wherein the thermosensitive polymer layer comprises a mixture or a chemical reaction product of a thermosensitive polymer and a cell-adhesive substance.

3. The bioreactor according to claim 1, wherein the spacer comprises a plurality of plastic rods.

4. The bioreactor according to claim 1, wherein the spacer is a fibrous nonwoven fabric.

5. The bioreactor according to claim 1, wherein the culture medium recovering porous tube has a pore size of 200-2,000 μm.

6. The bioreactor according to claim 1, wherein the porous sheet-form material is a PTFE sheet having its surface, which is hydrophilized with a polyamino acid/urethane copolymer, covered with poly-N-isopropylacrylamide.

7. The bioreactor according to claim 2, wherein the thermosensitive polymer is chemically bonded to the hydrophilized surface of the porous sheet-form material.

8. The bioreactor according to claim 2, wherein the cell-adhesive substance is chemically bonded to the hydrophilized surface of the porous sheet-form material.

9. The bioreactor according to claim 2, wherein the spacer comprises a plurality of plastic rods.

10. The bioreactor according to claim 2, wherein the spacer is a fibrous nonwoven fabric.

11. The bioreactor according to claim 7, wherein the cell-adhesive substance is chemically bonded to the hydrophilized surface of the porous sheet-form material.

12. The bioreactor according to claim 7, wherein the spacer comprises a plurality of plastic rods.

13. The bioreactor according to claim 7, wherein the spacer is a fibrous nonwoven fabric.

14. The bioreactor according to claim 8, wherein the spacer comprises a plurality of plastic rods.

15. The bioreactor according to claim 8, wherein the spacer is a fibrous nonwoven fabric.

16. The bioreactor according to claim 11, wherein the spacer comprises a plurality of plastic rods.

17. The bioreactor according to claim 11, wherein the spacer is a fibrous nonwoven fabric.

18. A method for culturing cells, the method comprising, in the bioreactor according to claim 1, making cells adhere to or become attached to the porous sheet-form material, culturing the cells while supplying a culture medium from at least one culture medium inlet port formed in the reactor main body, passing it through the culturing space and then through the culture medium-recovering porous tube, and making the culture medium flow out from the culture medium outlet port communicating with one end of the porous tube, and subsequently destroying the thermosensitive polymer layer of the porous sheet-form material under conditions in which the temperature is higher or lower than the culture temperature to thus recover the cells and/or cell secretions.

* * * * *